United States Patent [19]

Blanding et al.

[11] Patent Number: 4,512,952
[45] Date of Patent: Apr. 23, 1985

[54] APPARATUS FOR STORING AND DISPENSING ANALYSIS SLIDES

[75] Inventors: Douglass L. Blanding, Rochester; Martin F. Muszak, Spencerport, both of N.Y.

[73] Assignee: Eastman Kodak Company, Rochester, N.Y.

[21] Appl. No.: 394,193

[22] Filed: Jul. 1, 1982

[51] Int. Cl.³ ............................................ G01N 35/00
[52] U.S. Cl. .......................................... 422/63; 422/64; 422/66; 436/46; 414/119; 414/417
[58] Field of Search ................................ 422/63–67; 221/113, 119, 121, 232; 414/119, 417; 436/46

[56] References Cited

U.S. PATENT DOCUMENTS

| | | | |
|---|---|---|---|
| 3,574,064 | 4/1971 | Binnings et al. | 422/65 |
| 3,921,788 | 11/1975 | Roberson, Jr. et al. | 414/417 |
| 3,992,158 | 11/1976 | Przybylowicz et al. | 422/57 |
| 4,053,381 | 10/1977 | Hamblen et al. | 204/195 M |
| 4,152,390 | 5/1979 | Nosco et al. | 422/65 |
| 4,224,032 | 9/1980 | Glover et al. | 422/65 |
| 4,234,540 | 11/1980 | Ginsberg et al. | 422/67 |
| 4,276,051 | 6/1981 | Ginsberg et al. | 422/64 |
| 4,276,258 | 6/1981 | Ginsberg et al. | 422/67 |
| 4,296,070 | 10/1981 | Montalto et al. | 422/65 |
| 4,311,667 | 1/1982 | Gocho | 422/64 |
| 4,339,221 | 7/1982 | Mitzel et al. | 414/417 |

Primary Examiner—Michael S. Marcus
Attorney, Agent, or Firm—Dana M. Schmidt

[57] ABSTRACT

A method and apparatus are disclosed for storing and dispensing analysis slides in a chemical analyzer. Slides contained in cartridges are loaded into a rotor in a slide supply, and a positioning means is adapted to locate a selected cartridge such that a slide can be removed from the cartridge by a dispense blade. The blade is adapted to deliver the slide to a slide distributor in the analyzer.

11 Claims, 6 Drawing Figures

APPARATUS FOR STORING AND DISPENSING ANALYSIS SLIDES

BACKGROUND OF THE INVENTION

1. Field of the Invention

This invention relates to the chemical analysis of substances, and more particularly, to a method and apparatus for storing analysis slides on an analyzer and for delivering analysis slides to a slide distributor in the analyzer.

2. State of the Prior Art

Recent developments have provided analysis slides for use in performing quantitative analyses of biological fluids. The slides are essentially planar, contain reagents in dry form, and can be loaded into a cartridge for use in a chemical analyzer. In the operation of such an analyzer, an analysis slide is fed from a cartridge into a metering station where a predetermined amount of sample fluid is deposited on the analysis slide. After an appropriate incubation period, the slide is moved to an analysis station where a change in the slide is sensed, the amount of change being proportional to a particular analyte in the sample fluid. The slide is used only once and is discarded after the reading is taken. An analyzer for use with slides of this type is described in commonly-assigned U.S. Pat. No. 4,296,070, granted on Oct. 20, 1981.

In performing analyses, as described above, a different type of slide is needed for each of the analytes. Thus, in an analyzer of the type described, a cartridge of analysis slides must be carried on the analyzer for each of the desired tests, or assays. In high-throughput analyzers performing a large number of different tests, it may be necessary to store as many as fifty cartridges, each cartridge containing slides for a particular test. There is a problem in storing so many cartridges in a limited space and in such a manner that a slide can be removed from a selected cartridge for a desired test. In prior art devices, cartridges have been mounted on a turntable and the turntable is rotated to move a selected cartridge into an unload station. Such a device is shown in U.S. Pat. No. 4,224,032. In the device disclosed in this patent, however, the cartridges can only be mounted in a single ring on the outer periphery of the turntable, since the cartridges must cooperate with a slide feeding mechanism located radially inward of the cartridges. Thus, the number of cartridges which can be mounted on the turntable is limited.

It is an object of the present invention to overcome the above-described problems in prior art devices and to provide a novel method and apparatus for storing a relatively large number of cartridges in an analyzer and for dispensing slides from the cartridges.

In accordance with the present invention there is provided in a chemical analyzer for measuring a characteristic of a sample fluid wherein the fluid is deposited on an analysis slide which is analyzed after an appropriate period of time, the combination comprising: means for supporting a plurality of stacks of slides adjacent each other, each of the stacks having a longitudinal axis; means for removing a slide from a selected stack, the removing means being movable along a path generally transverse to the axes; and means for positioning the selected stack and the removing means relative to each other and to the supporting means such that a slide from the selected stack is in a position to cooperate with the removing means.

In accordance with the present invention, there is also provided a method of dispensing analysis slides from a slide supply in a chemical analyzer, the method comprising the steps of: loading a plurality of stacks of slides onto a support means in the supply; positioning one of the stacks relative to the other stacks and to the support means such that a selected analysis slide in the one stack is accessible to a slide removal means; and removing the selected slide from the stack and delivering the slide to a slide distributor.

In one embodiment of the invention, concentric rings of cartridges are mounted on a rotor which can be driven to move cartridges to an unload station; at the unload station, a lift mechanism is provided to move a selected cartridge into a dispense position such that its uppermost slide is in the path of a dispense blade. The dispense blade is adapted to remove the slide from the cartridge and deliver the slide to a slide distributor.

The disclosed invention is particularly advantageous for use in analyzers in which a large number of cartridges of slides are stored on the analyzer and each of the cartridges must be quickly and easily accessible for the removal of a selected slide. The cartridges are supported in a rotor, and the slide removal means is located relative to the rotor such that substantially the entire rotor can be used for storing cartridges.

DESCRIPTION OF THE PREFERRED EMBODIMENT

The invention is described hereinafter in connection with an analyzer for performing quantitative chemical analyses of biological fluids, such as blood serum. However, the invention is not so limited, and it can also be used in other types of apparatus in which a large number of objects from which articles are dispensed must be stored in a relatively small space.

The invention is useful with analyzers in which the substrate which makes the test possible comprises a pair of electrodes selective to the ion activity of choice. Recent developments have provided the electrodes in essentially planar, dry form suitable for use in pairs in an analyzer. An example of such a test element is disclosed in the patent to Hamblen et al., U.S. Pat. No. 4,053,381, granted on Oct. 11, 1977. This patent describes a test element, or analysis slide, of the type which is used to potentiometrically designate the activity of ions in a liquid test solution.

The invention can also be used with other forms of test elements, as, for example, the element disclosed in the commonly-owned patent to Przbylowicz et al., U.S. Pat. No. 3,992,158, granted on Nov. 16, 1976. The test element disclosed in this patent is formed as a multi-layered element containing the necessary reagents for reaction with components of a biological fluid, such as blood serum, deposited thereon. Certain reactions colorimetrically produce a change in optical density in the element which is sensed by a reflectometer, the amount of light reflected from the element varying in accordance with the reaction and being indicative of the amount of a particular analyte present in the fluid.

Terms such as "up," "down," "lower," "vertical," "horizontal," and "bottom," as used herein, refer to the orientation of parts when the apparatus is positioned in its customary position of use.

Figure 1:
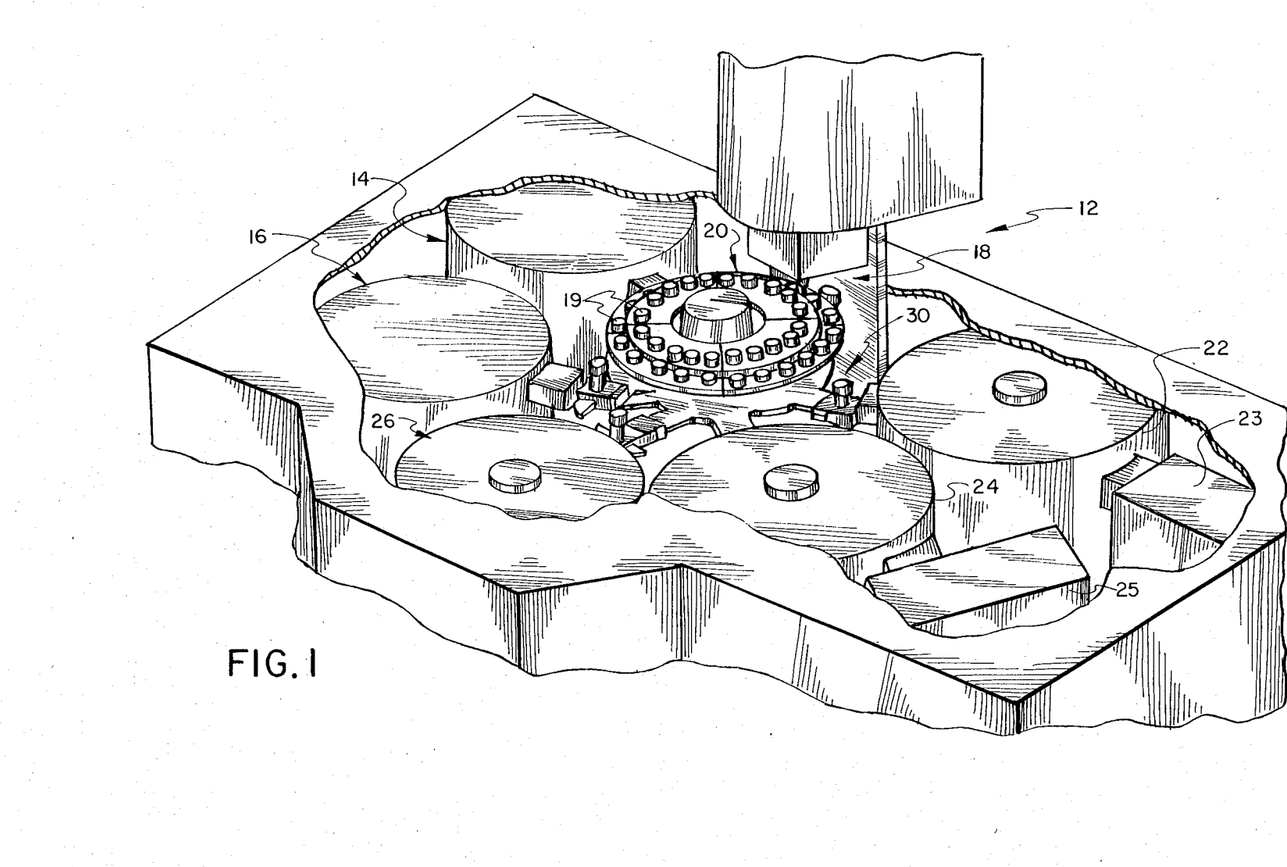
FIG. 1 is a perspective view of a chemical analyzer of the type which is adapted to employ the apparatus described herein.

In accordance with the preferred embodiment of the invention, there is shown in FIG. 1 an analyzer 12 of the type which is adapted to employ the apparatus described herein. Analyzer 12 comprises a slide supply 14 which is adapted to receive analysis slides 15 of the colorimetric type (FIG. 4), and a slide supply 16 which is adapted to receive analysis slides of the potentiometric type (not shown). Each sample fluid to be analyzed is supplied to analyzer 12 in a cup 19 which is supported on analyzer 12 in a tray 20. A metering device 18 is adapted to aspirate sample fluid from a selected cup 19 and to meter the fluid onto an analysis slide 15 in a slide distributor 30. A second metering device (not shown) works in conjunction with metering device 18 to deposit reference fluid on analysis slides of the potentiometric type. After the metering operation, analysis slides of the potentiometric type are delivered by distributor 30 to an incubator 22, and analysis slides 15 of the colorimetric type are delivered to an incubator 24. Incubators 22, 24, are adapted to cooperate respectively with analysis means 23, 25, for measuring changes in the analysis slides as a result of the fluid deposited thereon. Analysis slides 15 can also be used to perform rate analyses in which case they are delivered by distributor 30 to an incubator 26 where a series of readings are taken on each slide 15.

Preferably, slides 15 are supplied to analyzer 12 in a cartridge 34 (FIG. 4) which is adapted to receive a stack 17 of slides 15 disposed along a longitudinal axis 19. As shown in FIGS. 3–6, slide supply 14 comprises means for supporting a plurality of stacks 17 of slides 15 which includes a rotor 40 having cartridges 34 therein. As shown in FIG. 6, cartridges 34 are arranged in rotor 40 in an outer ring 35 and an inner ring 36; rings 35 and 36 are concentric. Such an arrangement permits a relatively large number of cartridges 34 to be stored in slide supply 14. An analysis slide 15 can be removed from a selected cartridge 34 by means which will be described hereinafter.

Figure 2:
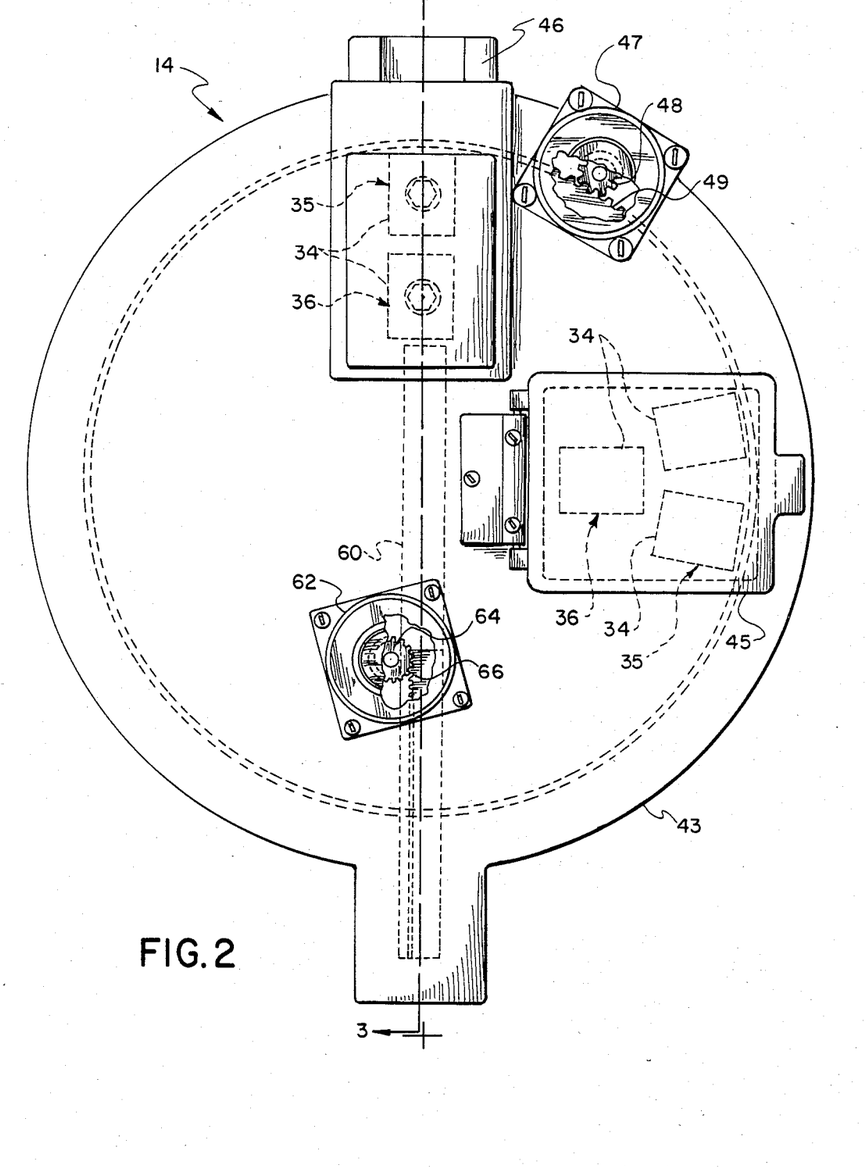
FIG. 2 is a top plan view of the slide supply showing the access door for loading and unloading cartridges and the dispense station.
Figure 3:
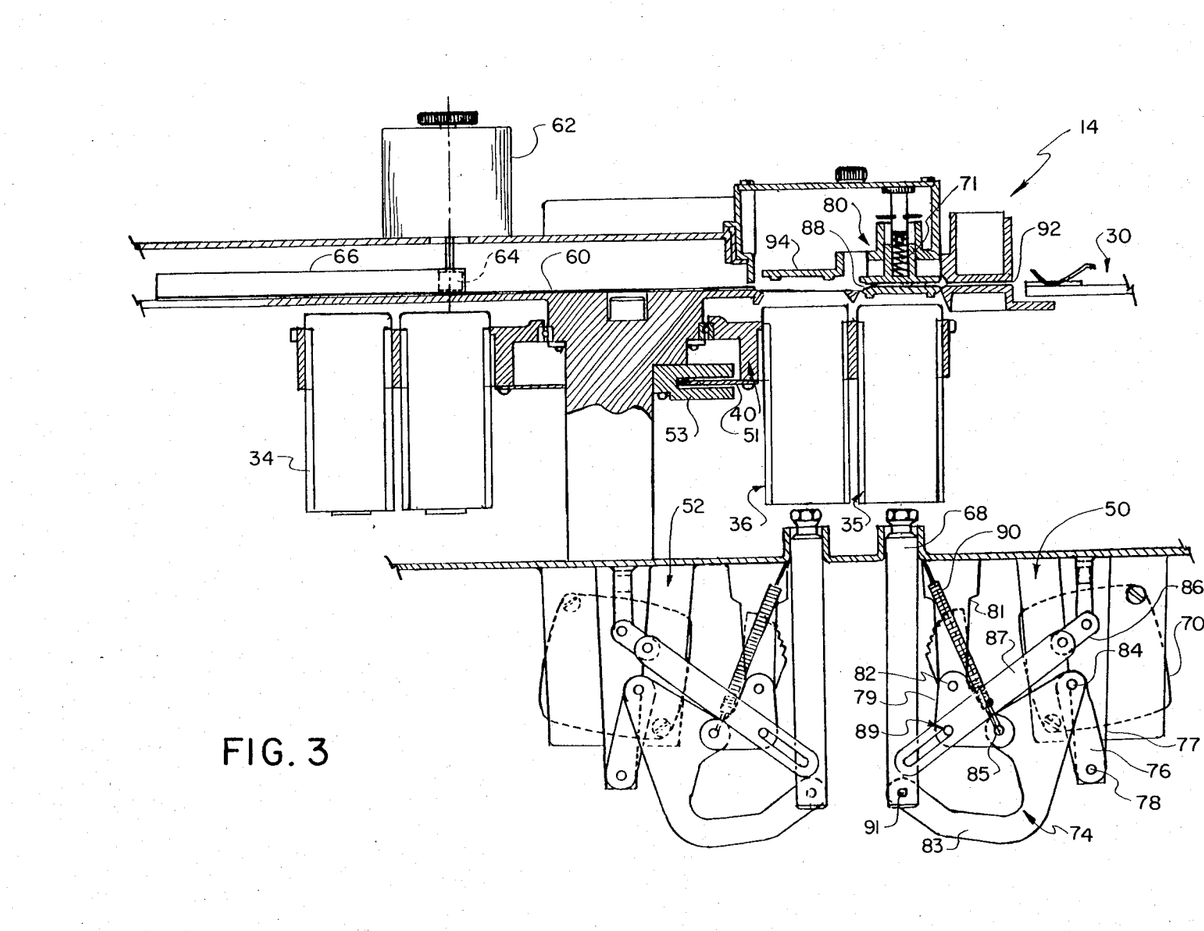
FIG. 3 is a sectional view taken along the line 3—3 in FIG. 2.
Figure 4:
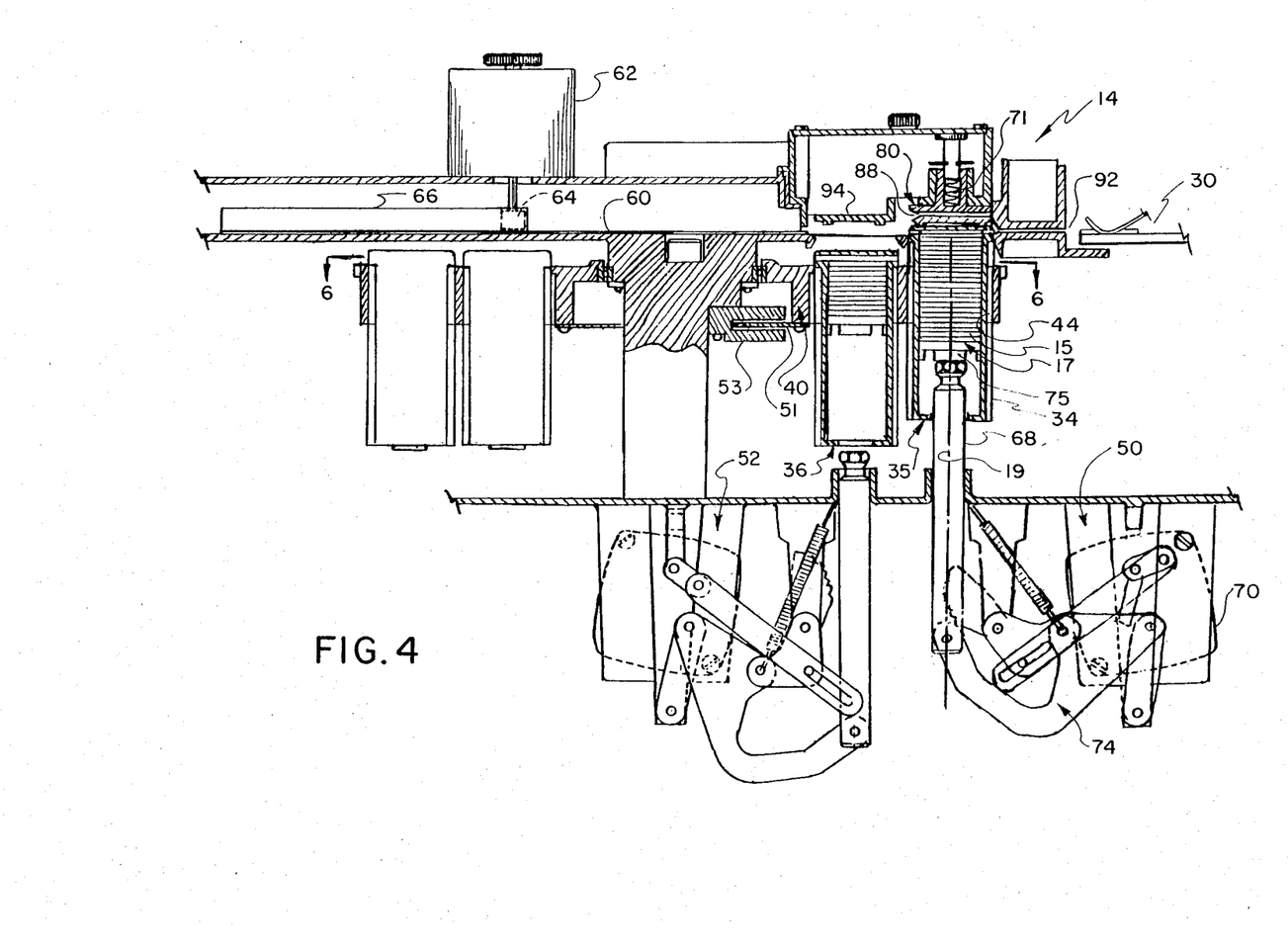
FIG. 4 is a view similar to FIG. 3, but showing a cartridge in the outer ring in the dispense position.

Rotor 40 is adapted to receive cartridges 34 in a plurality of nests 44 (FIG. 4). The inactive position of the cartridges is the position in which each cartridge is below the top of rotor 40, FIG. 3. Cartridges 34 can be loaded into rotor 40 and unloaded therefrom through an access door 45 (FIG. 2) in slide supply housing 43. Slides 15 are removed from a selected cartridge 34 at a dispense station 46 (FIG. 2). To position cartridges 34 in the dispense station 46 and to facilitate the loading and unloading of cartridges 34, rotor 40 is rotatable by a drive means which includes a motor 47 having a pinion 48 which meshes with a ring gear 49 on the rotor 40. An encoder disk 51 on rotor 40 (FIG. 4) is used to indicate the position of rotor 40 to a sensing device 53 which is adapted to effect the stopping of rotor 40 in the desired position. When slide supply 14 is used in analyzer 12, the position of each cartridge 34 and the type of slide contained therein is contained in memory in the analyzer computer (not shown). By techniques well known in the art, rotor 40 can be controlled to deliver a cartridge containing analysis slides 15 for a desired test to the dispense station 46.

After rotor 40 has delivered a selected cartridge 34 to the dispense station 46, a positioning means is adapted to move the selected cartridge 34 up into the dispense position in which the cartridge 34 is elevated relative to the other cartridges 34 in rotor 40. A cartridge 34 in the dispense position is shown in outer ring 35 in FIG. 4 and in inner ring 36 in FIG. 5. The positioning means includes a pair of lift mechanisms 50, 52, which cooperate with the cartridges 34. Means for removing a slide 15 from a cartridge 34 in the dispense position comprises a dispense blade 60 which is reciprocatively driven by a motor 62; motor 62 drives a pinion 64 which meshes with a rack 66 connected to blade 60. As shown in FIG. 4, blade 60 is movable along a path which is generally transverse to axis 19 and which lies in a plane removed from the location of the stacks of slides when the cartridges are in their inactive position. Preferably this plane is located above rotor 40; as a result of locating the slide removal means above the rotor 40, substantially the entire rotor 40 can be filled with cartridges 34.

Lift mechanism 50 comprises a plunger 68 which is driven by a synchronous motor 70. Motor 70 is connected to plunger 68 by means of a linkage 74 which is adapted to move plunger 68 in a straight line and to deliver a substantially constant force on the cartridge 34.

Linkage 74 comprises a first link 76 which is pinned to analyzer frame member 77 at 78 and a second link 79 which is pinned to analyzer frame member 81 at 82. A third link 83 connects links 76 and 79 and is pinned to plunger 68 at 91; link 83 is joined to link 76 at 84 and to link 79 at 85. Motor 70 is adapted to rotate an arm 86 in a clockwise direction. Arm 86 is pivotally connected to an element 87 which is connected to link 79 through a pin-and-slot connection 89. A coil spring 90 is connected to link 79 at 85 and serves to bias plunger 68 upwardly.

In the operation of lift mechanism 50, motor 70 positions arm 86 in a bottom-dead-center position, as shown in FIG. 3, to retract plunger 68. When it is desired to move plunger 68 up into a cartridge 34, as shown in FIG. 4, arm 86 is rotated clockwise from the bottom-dead-center position. When arm 86 has rotated to the position shown in FIG. 4, element 87 has been moved upwardly by arm 86; upward movement of element 87 permits spring 90 to move plunger 68 up into contact with follower member 75 in cartridge 34. Changes in the compressive force of spring 90 are compensated by a change in moments of the linkage 74 such that a substantially constant force is delivered by plunger 68 onto follower member 75. For a cartridge 34 of slides 15, as described in the aforesaid U.S. Pat. No. 3,992,158, a substantially constant force of ten ounces on member 75 has been found sufficient to position cartridge 34 in the dispense position, and yet not place excessive axial force on the slides 15. Removing the slides from cartridge 34 is difficult, if the axial force on the slides 15 is too great.

To dispense an analysis slide 15 from a cartridge 34 in the outer ring 35, motor 70 is actuated to advance plunger 68 into contact with follower member 75 in cartridge 34, as shown in FIG. 4. Upward movement of plunger 68 moves cartridge 34 into the dispense position and up against a platen 80. Platen 80 is biased downwardly by a spring 71. Movement of cartridge 34 to the dispense position moves platen 80 upward to the position shown in FIG. 4 and places the uppermost analysis slide 15 in the cartridge 34 in the plane of blade 60 and in a position to be moved out of cartridge 34 by blade 60. When plunger 68 of lifting mechanism 50 is returned to the position shown in FIG. 3, cartridge 34 moves down and platen 80 also moves down such that a passageway 88 in platen 80 is in line with the path of movement of dispenser blade 60.

Figure 5:
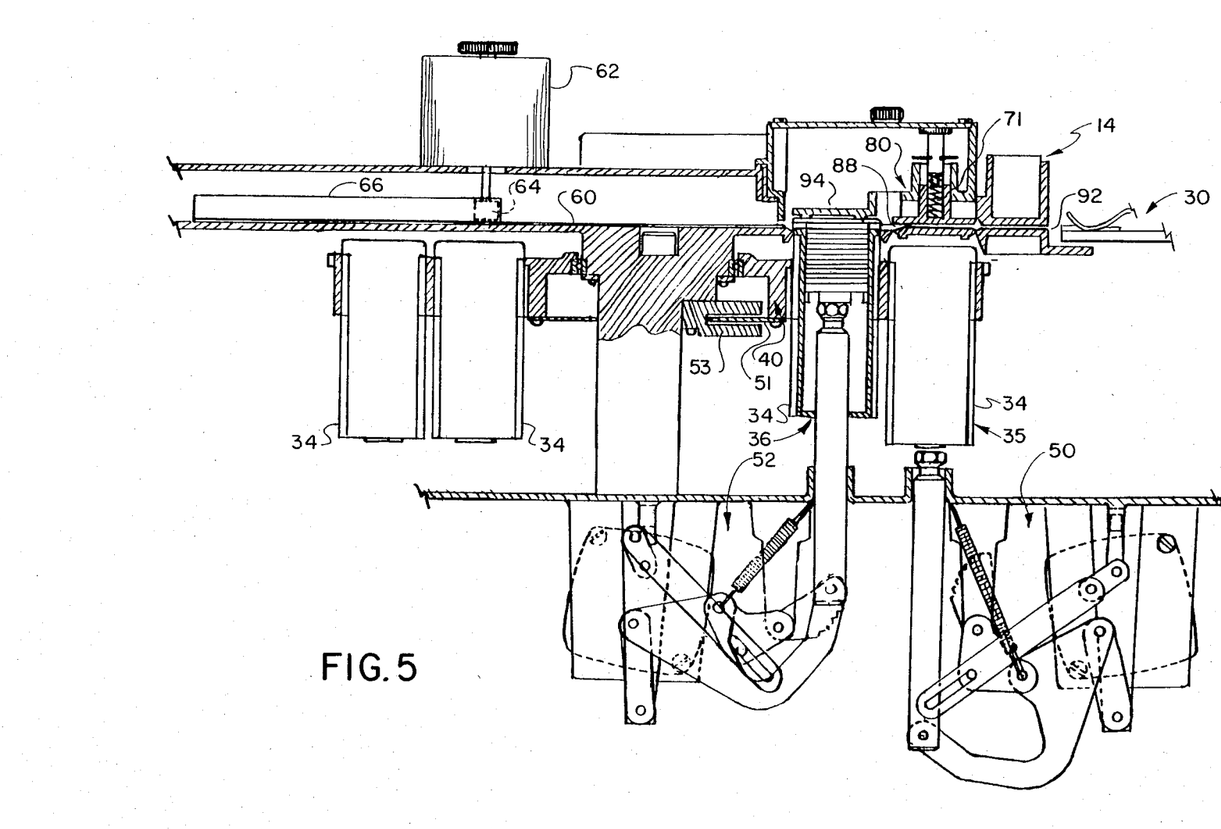
FIG. 5 is a view similar to FIGS. 3 and 4, but showing a cartridge in the inner ring in the dispense position.
Figure 6:
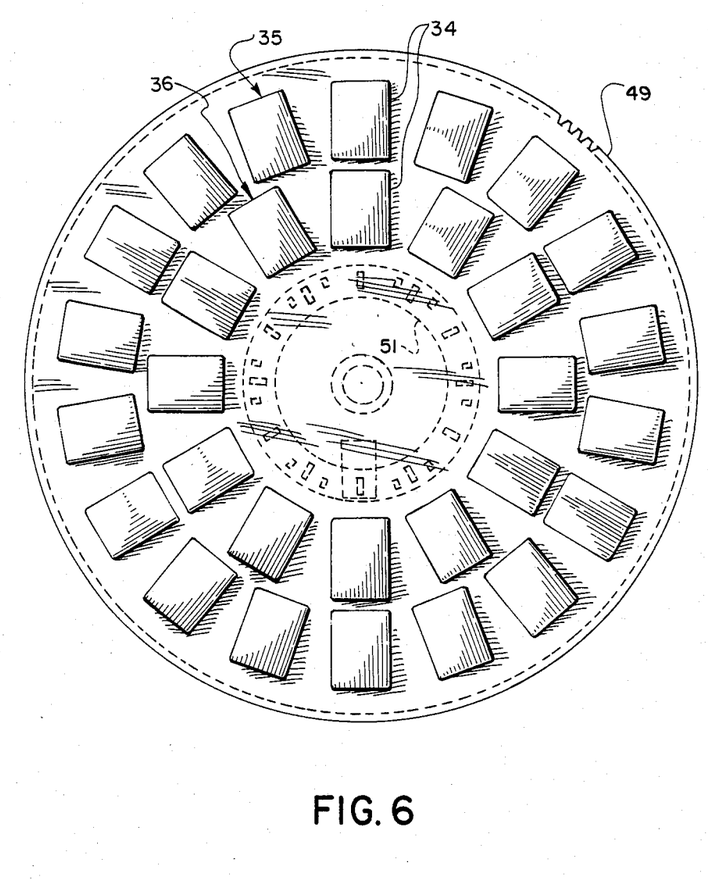
FIG. 6 is a sectional view, taken along the line 6—6 in FIG. 4.

With the platen 80 in the downward position, as shown in FIGS. 3 and 5, track means are provided to dispense a slide from a cartridge 34 in the inner ring 36 of cartridges 34 over the adjacent cartridge in the outer ring. Specifically, platen 80 noted above functions as the track means, and moves along the axis of cartridge 34 in accordance with the movement of that cartridge. To dispense an analysis slide 15 from the inner ring 36, a cartridge 34 in ring 36 is elevated by lift mechanism 52 to the dispense position, as shown in FIG. 5. Lift mechanism 52 is identical to lift mechanism 50 and functions in the manner described above for lift mechanism 50. As shown in FIG. 5, when a cartridge 34 in the inner ring 36 is in the dispense position, the cartridge is resting against a stop 94. When the cartridge 34 in ring 36 is in the dispense position, motor 62 is actuated to move dispenser blade 60 from left to right, as viewed in FIG. 5. As blade 60 moves to the right, a slide 15 from a cartridge 34 in ring 36 is first moved into passageway 88, then into a guide 92 at dispense station 46, and finally into slide distributor 30, positioned as shown in FIG. 3.

Slides removed from a cartridge 34 in ring 35 are first moved by blade 60 into guide 92 and then into slide distributor 30. Slide distributor 30 delivers slides to the various components of analyzer 12 as described in the aforesaid U.S. Pat. No. 4,296,070.

The invention has been defined in detail with reference to certain preferred embodiments thereof, but it will be understood that variations and modifications can be effected within the spirit and scope of the invention.

What is claimed is:

1. In a chemical analyzer for measuring a characteristic of a sample fluid wherein the fluid is deposited on an analysis slide which is analyzed after an appropriate period of time, the analyzer including
    means for supporting a plurality of stacks of slides adjacent each other, each of said stacks having a longitudinal axis;
    means for removing a slide from a selected stack, said removing means being movable along a path generally transverse to said axes; and
    means for positioning said selected stack and said removing means relative to each other and to said supporting means such that a slide from the selected stack is in a position to cooperate with said removing means;
    the improvement wherein
    (a) said supporting means mounts said stacks in concentric rings with said slides of each stack being movable into and out of the plane of said removing means path, at least some of the stacks of one of said rings being positioned so that, when such one ring stacks are moved into the plane of said removing means path, they block the slides of a stack of the other ring from being removed by said removing means,
    (b) said positioning means comprise means for selectively moving said selected stacks into the plane of said path,
    (c) and movably mounted track means are cooperatively positioned with respect to the stacks of said one ring to provide a pathway for removal of slides from the stacks of said other ring when said one ring stacks are moved out of the plane of said removing means path, said track means being mounted to move along the same axis as, and in response to the movement of, said stacks of said one ring.

2. The combination, as defined in claim 1, wherein said positioning means comprises a plunger adapted to effect movement of said selected stack.

3. The combination, as defined in claim 1, wherein said removing means comprises a dispense blade mounted for reciprocation.

4. The combination, as defined in claim 1, wherein said supporting means includes a rotor and said stacks are vertically disposed on said rotor, and said positioning means comprises means for moving one of said stacks vertically relative to the others.

5. The combination, as defined in claim 1, wherein each of said stacks is enclosed in a cartridge which is positionable by said positioning means.

6. In a slide supply for use in a chemical analyzer of the type in which fluid is metered onto an analysis slide which is analyzed after an appropriate period of time, said supply comprising:
    means for receiving a plurality of stacks of slides and for delivering a selected stack to a dispense station;
    means for removing a slide along a predetermined path, from said stack in the dispense station; and
    means for positioning said stack in the dispense station relative to the other stacks to place said stack in a position to cooperate with said removing means;
    the improvement wherein
    (a) said supporting means mounts said stacks in concentric rings with said slides of each stack being movable into and out of the plane of said removing means path, at least some of the stacks of one of said rings being positioned so that, when such one ring stacks are moved into the plane of said removing means path, they block the slides of a stack of the other ring from being removed by said removing means,
    (b) said positioning means comprise means for selectively moving said selected stacks into the plane of said path,
    (c) and movably mounted track means are cooperatively positioned with respect to the stacks of said one ring to provide a pathway for removable of slides from the stacks of said other ring when said one ring stacks are moved out of the plane of said removing means path, said track means being mounted to move along the same axis as, and in response to the movement of said stacks of said one ring.

7. A slide supply, as defined in claim 6, wherein said removing means comprises a dispense blade and means for reciprocating said blade.

8. A slide supply, as defined in claim 6, wherein each of said stacks is enclosed in a cartridge, and said receiving means is a rotor having a plurality of nests for receiving cartridges.

9. A slide supply, as defined in claim 8, wherein drive means is coupled to said rotor for delivering said selected stack to the dispense station.

10. A slide supply, as defined in claim 6, wherein said positioning means comprises a lift mechanism operatively engageable with said stack in the dispense station.

11. A slide supply, as defined in claim 10, wherein said lift mechanism comprises a plunger operatively engageable with a stack, a drive motor, and a linkage coupling said motor to said plunger, said linkage being adapted to produce a substantially constant force on said stack.

* * * * *

UNITED STATES PATENT AND TRADEMARK OFFICE
CERTIFICATE OF CORRECTION

PATENT NO. : 4,512,952
DATED : April 23, 1985
INVENTOR(S) : D.L. Blanding and M.F. Muszak It is certified that error appears in the above-identified patent and that said Letters Patent is hereby corrected as shown below:

Claim 6, line 57, delete "removable" and insert --removal--.

Signed and Sealed this

Eighth Day of January, 1991

Attest:

HARRY F. MANBECK, JR.

*Attesting Officer*  *Commissioner of Patents and Trademarks*